(12) United States Patent
Bush (10) Patent No.: US 10,292,860 B2
(45) Date of Patent: May 21, 2019

(54) THERMAL THERAPY SHEET

(71) Applicant: Richard W. Bush, Honolulu, HI (US)

(72) Inventor: Richard W. Bush, Honolulu, HI (US)

( * ) Notice: Subject to any disclaimer, the term of this patent is extended or adjusted under 35 U.S.C. 154(b) by 0 days.

(21) Appl. No.: 14/975,229

(22) Filed: Dec. 18, 2015

(65) Prior Publication Data

US 2017/0172787 A1 Jun. 22, 2017

(51) Int. Cl.
| | | |
|---|---|---|
| *A61F 7/00* | (2006.01) | |
| *A61F 7/02* | (2006.01) | |
| *A61H 39/04* | (2006.01) | |

(52) U.S. Cl.
CPC .............. *A61F 7/02* (2013.01); *A61F 7/0097* (2013.01); *A61H 39/04* (2013.01); *A61F 2007/0088* (2013.01); *A61F 2007/0244* (2013.01); *A61F 2007/0266* (2013.01); *A61H 2201/0207* (2013.01); *A61H 2201/0221* (2013.01); *A61H 2201/10* (2013.01); *A61H 2201/165* (2013.01); *A61H 2201/1695* (2013.01)

(58) Field of Classification Search
CPC .................................. A61F 7/02; A61H 39/04
See application file for complete search history.

(56) References Cited

U.S. PATENT DOCUMENTS

| | | | |
|---|---|---|---|
| 2,787,266 A | 4/1954 | Scholl | |
| 3,033,201 A | 5/1962 | Olsen | |
| 3,255,749 A | 6/1963 | Smithers | |
| 3,892,239 A * | 7/1975 | Remiro | A61F 13/06 601/1 |
| 4,084,586 A | 4/1978 | Hettick | |
| 4,121,582 A | 10/1978 | Remiro | |
| 4,378,009 A | 3/1983 | Rowley | |
| 4,753,241 A * | 6/1988 | Brannigan | A61F 7/02 156/210 |
| 4,832,010 A | 5/1989 | Lerman | |
| 4,911,155 A | 3/1990 | Delannoy | |
| 4,961,418 A | 10/1990 | McLaurin-Smith | |
| 5,158,073 A * | 10/1992 | Bukowski | A61H 39/04 5/944 |
| 5,250,067 A | 10/1993 | Gelfer | |
| 5,503,908 A | 4/1996 | Faass | |
| 5,599,283 A | 2/1997 | Lindenmeyer | |
| 5,679,052 A | 10/1997 | Rucki | |
| 5,728,146 A | 3/1998 | Burkett | |
| 5,904,710 A | 5/1999 | Davis | |
| 5,906,637 A | 5/1999 | Davis | |
| 5,938,684 A | 8/1999 | Lynch | |
| 5,976,099 A | 11/1999 | Kellogg | |
| 6,048,326 A | 4/2000 | Davis/Cramer | |
| 6,313,370 B1 | 11/2001 | Hyson | |
| 6,336,965 B1 | 1/2002 | Davis | |
| 6,520,926 B2 | 2/2003 | Hall | |

(Continued)

*Primary Examiner* — Kristen Matter (57) ABSTRACT

A device and method used to help reduce aches and pains to joints, muscles, and other body parts; helps to relieve swelling; provide support to joints and muscles. Comprising of a plurality of ridges 120 affixed to a flexible thermal sheet 110. Said ridges 120 produce an acupressure-like massage effect and the flexible thermal sheet 110 absorbs and reradiates heat between the device and skin producing a self-heating effect. The device can be sized for a particular application. A user places the device against his or her body part and device is held in place by a method of user's choice.

6 Claims, 7 Drawing Sheets

(56) References Cited

U.S. PATENT DOCUMENTS

| | | |
|---|---|---|
| 6,508,776 B2 | 5/2003 | Chiang |
| 6,726,641 B2 | 4/2004 | Chaing |
| 7,135,007 B2 | 11/2006 | Scott |
| 7,223,252 B2 * | 5/2007 | Takahashi ................ A61H 7/00 601/134 |
| 7,273,464 B2 | 9/2007 | Reinhardt |
| 7,767,874 B2 | 8/2010 | Kellogg |
| 7,878,187 B2 | 1/2011 | York-Leung |
| 2003/0124277 A1 | 12/2003 | Agarwal |
| 2005/0039349 A1 * | 2/2005 | Grisoni ................ A43B 7/1425 36/71 |
| 2005/0124925 A1 * | 6/2005 | Scherpenborg ........... A61F 7/02 602/41 |
| 2006/0004308 A1 * | 1/2006 | Yamauchi ............... A61H 39/04 601/28 |
| 2007/0185527 A1 * | 8/2007 | Babaev ............. A61B 17/1325 606/204 |
| 2008/0071205 A1 | 3/2008 | Howard |
| 2009/0036999 A1 | 2/2009 | Egilssson |
| 2013/0035217 A1 * | 2/2013 | Beck ...................... A63B 23/04 482/79 |
| 2013/0131563 A1 | 5/2013 | Ettner |
| 2013/0254971 A1 | 10/2013 | Galluzzo |
| 2014/0024984 A1 * | 1/2014 | Allen ..................... A61H 7/007 601/134 |
| 2014/0142614 A1 | 5/2014 | Gallagher |
| 2014/0163482 A1 | 6/2014 | Leyva |
| 2016/0287472 A1 * | 10/2016 | Starzhynskaya ....... A61H 39/04 |

* cited by examiner

THERMAL THERAPY SHEET

FIELD OF INVENTION

This disclosure relates to a device and methods used to help reduce aches and pains to joints, muscles, and other body parts; help relieve swelling; provide support to joints and muscles.

DESCRIPTION OF PRIOR ART

The common treatment of arthritis; aches and pains to joints and muscles; sprains; swelling; nerve, ligament, tendon discomfort are commonly treated with compression apparatus, heat applications/apparatus, manual human massage and apparatus used to massage, apparatus to apply pressure at pressure points, braces and supports, wraps, apparatus impregnated with medication(s), oral and injected medicine.

The remedies to help relieve body aches and pains are immense. External Heat is a known remedy to help relieve aches and pains of the body. Electrical heating pads are a common method but need electricity and limit a user's mobility. Gels and thermal packets need to be heated prior to application. Exothermic composition which generates heat when exposed to oxygen is used only one time and disposed of.

Medications can be ingested with varying results and side effects.

Flexible elastomeric compression-supports are typically shaped to selectively conform to a portion of a user's body. Multilayered compression-supports are designed to avoid bunching or inadvertent overlapping, which causes discomfort for users. Additionally, various forms of fabric liner are typically used to enhance the user's experience.

Massage and acupressure are a proven method to help relieve pain but require a specialist to administer treatment. Not only are the treatments expensive and time consuming, results vary on the level of specialist's expertise. An electric hand held massager is another form of massage but requires electricity.

Elastic bandage material can be used in many forms for compression and support. Elastic bandages can be used as a stand-alone compression device and support. Their design comes in many forms, from a tailored and sized device for a selective body area, to a simple rolled bandage ready for application on a selected body part. Garments can be made of elastic bandage material, but are limited because they are sized for a particular application.

Adhesive tape is another form of compression and support for a selected body area of user, and used extensively in sports. Not only does a user have the daily expense for adhesive tape, but the user's skin needs to be prepped prior to applying adhesive tape.

Rigid braces are another form of support, but are made specifically for a selected body area of user. Although a brace provides support, it may not provide compression.

Some prior approaches to reduce arthritic discomfort, reduce aches and pains to muscles and joints, reduce swelling, provide muscle and joint support, apply compression to a selective area include the following patents:

U.S. Pat. No. 7,767,874, issued to Kellogg, for "Medical Device and Process." This device claims removal of excess fluids from body tissue. The device is based upon elongated pockets, which create a high pressure area, whereby the pressure in the high pressure area creates low pressure flow channels. Also, the device is a multilayered assembly including stitching and small chopped foam having a maximum span and size that is smaller than its layers. As a multilayered assembly, the devise must be sized and shaped for each application.

U.S. Pat. No. 5,976,099 A, issued to Kellogg, for "Method and Apparatus to Medically Treat Soft Tissue Damage, Lymphedema and Edema." The device is based upon an enclosure holding a multiplicity of elongated pockets being separated from one another by a multiplicity of seams, and a bladder is used for compression.

U.S. Pat. No. 6,048,326, issued to Cramer, for "Exothermic Heat Cells Are Utilized to Generate Heat and Spaced Apart for Flexibility." This invention relates to heat cells and disposable elastic which conforms to user's knee.

Patent US 20030124277, issued to Agarwal, for "Elastic Thermal Wrap." Wrap consists of thermal pockets which can be heated or refrigerated Patent WO 2001080797 A1, issued to Morton I Hyson, for "Medicated wrap" is a wrap with inwardly extending nodule adapted to exert acupressure and compress a specific area, impregnated with medication.

U.S. Pat. No. 4,961,418A, issued to McLaurin-Smith, for "Heat Retaining Fabric and Physical Therapy Appliance." It has an inner layer which directly contacts the user's skin, is a knitted nylon fabric with interwoven yard to form a loop pile which contacts and stimulates the user's skin.

Patent CA2380661C, issued to Ouellette, for "Elastic Knee Wrap." The wrap includes a plurality of thermal elements embedded in the piece of flexible web. The plurality of thermal elements has a pattern which applies thermal energy to the sides and top of the user's knee.

U.S. Pat. No. 5,904,710 A, issued to Davis, for "Disposable Elastic Thermal Body Wrap." This invention relates to disposable elastic thermal body wraps having an elastic laminate structure formed from a polymeric mesh and two fabric carrier layers, and one or more heat cells.

U.S. Pat. No. 3,892,239, issued to Remiro, for "Quinohydrothermic Body Covering Element." It is a heat retaining stratified material which includes a thin layer of rubber with a laminar construction which decreases in section progressively in one direction. The thin layer of rubber is intimately associated with another layer which is of knitted fabric.

U.S. Pat. No. 4,121,582, also issued to Remiro, for "Direct Body Covering Sheet Having A Correcting and/or Therapeutic Action." It is a fabricated sheet structure apparently substantially similar to that disclosed in U.S. Pat. No. 3,892,239. The layer of rubber is thicker at the widest part of the garment and thinner at the narrowest part thereof, and used for the construction of garments. It consists of 3 elements: fabric sheet on the outside, latex layer in the middle, and fabric sheet on the inside.

U.S. Pat. No. 6,520,926 B2, issued to Michael Hall, for "Compression Support Sleeve." In this sleeve a substantial portion of one of the elastomeric polymer surfaces is coated with a discontinuous layer of silicone microdots. The spacing between said dots is to allow breathing through the layers of the support. The dots have a low profile with a thickness between about 1 to 4 mils, which could be the average thickness of a piece of human hair.

Patent No. 20140163482 A1, issued to Jacqueline Leyva, for "Figure Molding and Weight Loss Aid Systems and Methods." It is a garment comprising of an insulated panel and boning segment which is used in aiding weight loss and used for exercise. It is used to contact an anti-cellulite agent to the body.

Patent No. US20140142614 A1, issued to Ali Gallagher, for "Portable Mat." It describes a devise useful for temporarily reducing the appearance of cellulite and increasing local circulation. The user's own body weight is used to press the portable mat against the skin. The portable mat has a form factor that limits the portable mat application and is used sitting or when the user is lying on his side, on his back, or face down.

It would therefore be desirable to provide new and improved device and method for the common treatment of aches and pains to muscle, joints, and other body parts; help reduce swelling; support a joint or muscle. A device and method would be particularly desirable if able to overcome conventional shortcomings, including: the need for heating elements to generate heat, the need for fabrics intimately integrated into a device, the need to position a user in the right position to use a device, the flexibility to use a device on multiple body areas and on multiple types of applications, avoiding the need for concise sizing, ability of user to custom size a devise by simply cutting.

DESCRIPTION OF THE PRESENT INVENTION

The invention is a device that is held and/or pressed against a body part and may be used for the treatment of: arthritis; aches and pains to joints, muscles, and other body parts; swelling; and used to support a muscle and/or joint. The device is comprised of:

An outer component consisting of a flexible thermal sheet, which is pressed against a selective body part of user producing a reradiating heat effect, may support a joint or muscle, and may apply compression to a selective body part.

An Inner component consisting of a plurality of ridges, which are attached or molded to the flexible thermal sheet. The ridges produce an acupressure-like massage effect.

Heat is a known remedy for aliments of the body and has a healing effect. The device absorbs and reradiates heat between the device and skin because of its thermal conductivity properties. As a nonlimiting example, the ambient temperature is approximately 73 degrees Fahrenheit with an approximate mean skin temperature of 89 degrees Fahrenheit without using the device. Using the device, the skin temperature rises to approximately 95 degrees Fahrenheit providing the therapeutic effects of heat at the selected body part.

Said ridges of various or identical shape and various or identical size can be attached symmetrically on said flexible thermal sheet or said ridges placed randomly.

Said ridges contact the user's skin when ridges are spaced apart, spaced together, or intersect one another on the flexible thermal sheet.

The device must be sufficiently flexible to enable the device to surround a portion of the body part. Said ridges are of sufficient size to produce an indentation on the skin and the indentations disappear over time. In addition to the ridges producing an acupressure like massage effect, in said ridges that are elongated, the indentation will become channel-like, and thereby possibly providing a short-term evacuation channel for retained fluid of a body part. Elongated ridges arranged in a crisscrossing pattern provide additional therapy. As a user of the device, the performance and comfort of the device does not appear to be affected by bunching or overlapping of the device.

The ridges need not have thermal properties nor be of the same material as the flexible thermal sheet. The ridges may be formed and then mechanically, chemically or thermally bonded or joined to form the device. The ridges produce an acupressure-like massage effect which appears to provide additional relief for pain, discomfort, and swelling. The ridges may help reduce slippage of the device.

The device can be pressed and/or held against the user's body part at various locations and held in place with adhesive tape, elastic sleeve, strapping, or Velcro®. Said device may be used with other braces, supports, bandages, and wrappings. A stand-alone Ace Bandage (Trademarked) elastic bandage works well to hold and/or press the device against a body part. Pressing and/or holding the device in place is an individual preference. Other methods of pressing and or holding the device in place are possible.

The device can be cut to allow two opposing ends of the device to be connected to each other, creating a slip-on, tube like supporter for an arm, leg, knee, elbow or other body parts.

The device may act as a muscle and/or joint supporter. The device can be wrapped around a muscle or joint to support a specific area. Overlapping of the device can increase the device's support effectiveness. The thickness and hardness of the device can be adjusted for a more rigid supporter. The device can be cut to better accommodate a bent joint, breast, neck, shoulder, and other body part.

Said device may be stretched to provide compression to a selected body part.

The device can be a sheet or rolled as a bandage. The ridges can be on one side or both sides of the flexible thermal sheet. When the ridges are applied to both sides of the flexible thermal sheet, it can create a lock where the device overlaps itself and then pressure is applied.

The device is so simple; generally no sizing of the device is required. One size can fit all, but the device can simply be cut to size and be used in conjunction with existing orthopedic supports. The device can be placed between an existing orthopedic device and the user's body part or placed upon an existing orthopedic device such as a compression sleeve or fabric garment.

The device can be applied for a short period of time, but best results occur when the device is used for an extended period of time. It is preferable to use the device for periods greater than about 10 minutes. A hour is more preferable, preferably greater is 6 hours, more preferably greater than 9 hours, most preferable for 24 hours. During sleep is a preferred time to utilize this device.

BRIEF DESCRIPTION OF THE FIGURES

FIG. 5 A-B depicts a perspective view and top view of one embodiment of thermal therapy sheet 100 cut for an application against a user's breast.

LIST OF REFERENCE NUMERALS

100 Thermal Therapy Sheet (Device)
110 Flexible Thermal Sheet

120 Ridges
130 Hole cut or manufactured into Thermal Therapy Sheet 100
140 Cut or manufactured cut into Thermal Therapy Sheet 100

DETAIL DESCRIPTION

Embodiments disclosed herein provide a thermal therapy sheet 100 useful for the treatment of: arthritis; sprains; swelling; aches and pains to: joints, muscles, and other body parts, used as a joint and or muscle supporter.

Figure 1:
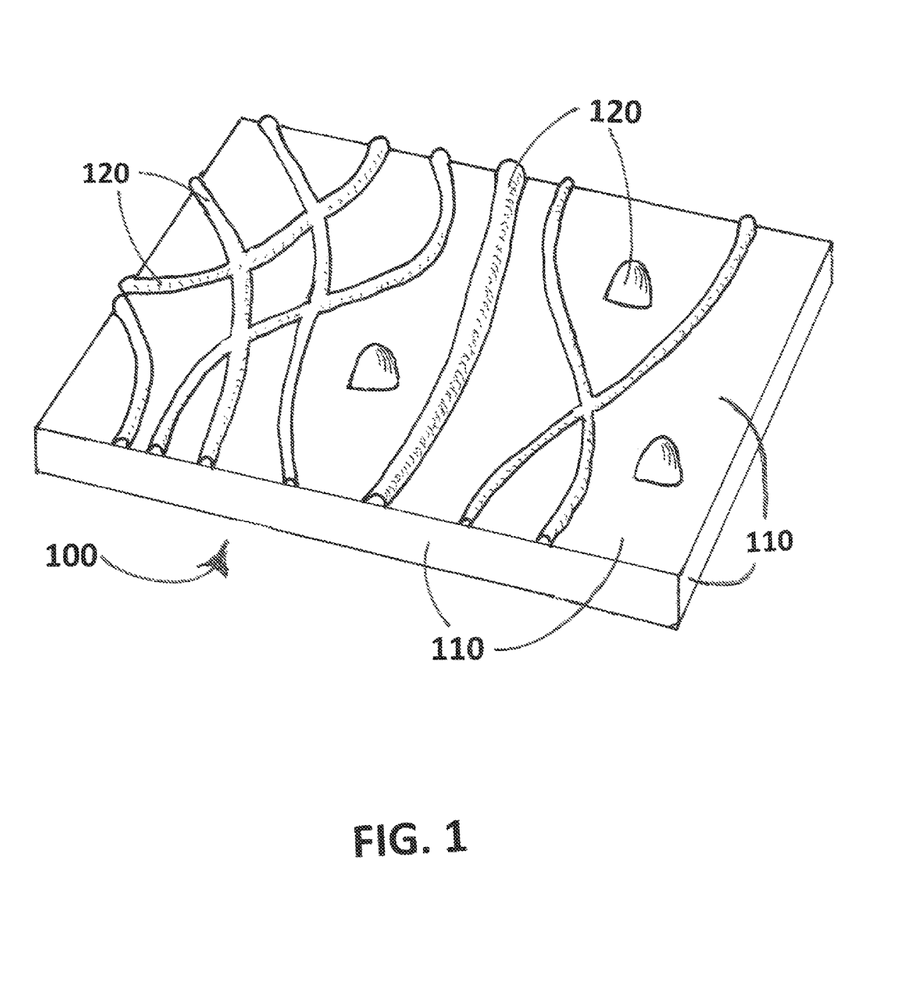
FIG. 1 depicts one embodiment of thermal therapy sheet with ridges attached to flexible thermal sheet.

FIG. 1 depicts perspective view of one embodiment, comprising of a flexible thermal sheet 110, and a plurality of ridges 120 attached to flexible thermal sheet 110.

In some embodiments, the flexible thermal sheet 110 may be of an elastomer material such as: silicone rubber, styrene butadiene, chloroprene, natural rubber, polyacrylate. Styrofoam, thermoplastic elastomers, and other solid flexible thermal heat reradiating materials are possible.

In some embodiments, the flexible thermal sheet 110 varies in thickness from approximately 0.025 inch to approximately 0.450 inch, a hardness or resilience of between approximately 5-95 Shore OO on a durometer, thermal conductivity between 0.01-0.60 W/(mK), and elasticity between approximately 100% to approximately 1500%. A material with 100% elasticity equals no stretching characteristics when pulled, whereas 1500% elasticity equals the material stretched to 15 times its resting length and/or width before failure.

The flexible thermal sheet 110 varies in thickness, hardness, thermal conductivity, and elasticity to accommodate an application. As a non-limiting example, a thicker, and or harder, and or less elasticity thermal sheet 110 may be more beneficial as a joint supporter than a thinner, and less hard, and or high elastic thermal sheet 110. A thinner, and less hard, and more elasticity thermal sheet 110 may be more beneficial for applying compression to help reduce swelling. A low thermal conductivity may be more beneficial to help relieve aches and pains.

Figure 2:
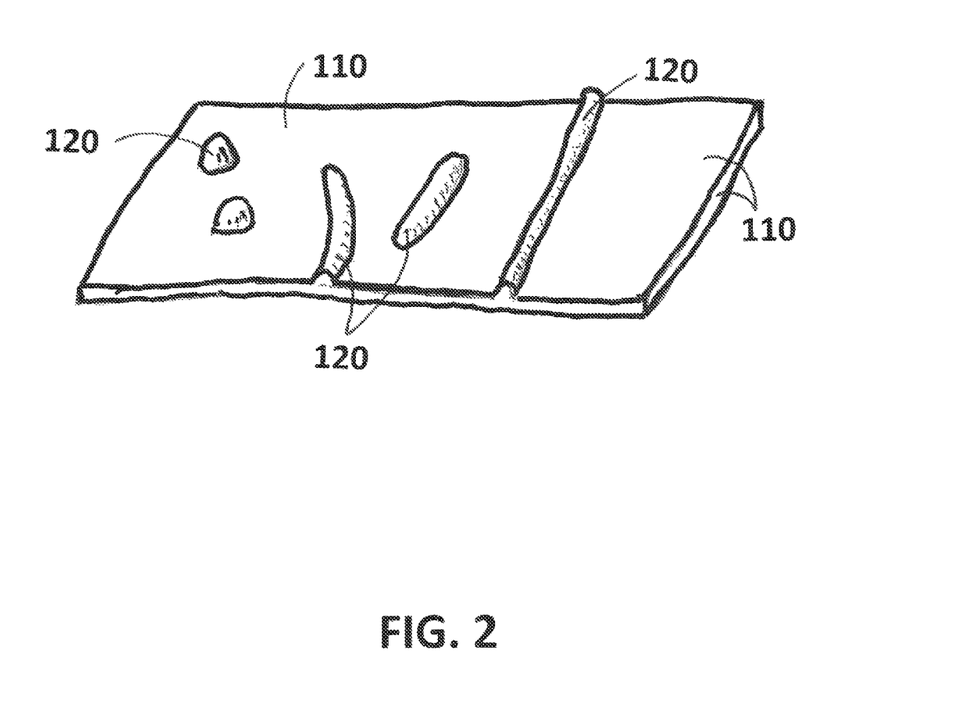
FIG. 2 depicts one embodiment of thermal therapy sheet with ridges molded to thermal sheet in a one-step monolithic process.

FIG. 2 depicts perspective view of one embodiment of thermal therapy sheet 100, ridges 120 and flexible thermal sheet 110 manufactured using a one-step monolithic manufacturing process.

In some embodiments, ridges 120 depicted in FIG. 1-7 produce an acupressure-like massage effect to help relieve aches and pains. The ridges 120 produce an indentation on the skin and may become a short evacuation channel for retained fluids of a body part. The indentations from the ridges 120 disappear over time.

The ridges 120 are of various or identical shape and various or identical size, attached symmetrically on the thermal material 120 or ridges 120 placed randomly. The ridge 120 may be as small as approximately 0.025 inch in width, approximately 0.025 inch in height, approximately 0.025 inch in length. The ridge 120 length may be greater than approximately 0.025 inches and may run the entire length or width of thermal sheet 120, may vary in width from approximately 0.025 inch to approximately 0.0625 inch, and may vary in height from approximately 0.025 inch to approximately 0.625 inch. The ridges 120 may be spaced together, spaced apart, intersect one another, or in any combination thereof.

In some embodiments, the ridges 120 may be made of same or different materials. One ridge 120 may be made of an elastomer and another made of plastic or a combination of both. For example, the ridge 120 may be made of wood, foam, metal, fiberglass, or a composite material. Other solid materials are possible.

The material for ridges 120 may be the same material as the flexible thermal sheet 110, which may simplify manufacturing to a one-step monolithic process. In some embodiments, the device may be made using an injection molding process. Other manufacturing processes are possible.

In some embodiments, flexible thermal Sheet 110 and ridges 120 may be formed from a silicone rubber such as R-1318, compounds A and B, available from Silpak, Inc. The mixed compounds provide elasticity, low thermal conductivity, joint and/or muscle support, and acupressure-like massage effect. The material is nearly impregnable to liquids and creams, and may be cleaned by hand. The compounds can be formed in a variety of colors. Other materials may be possible.

Figure 3:
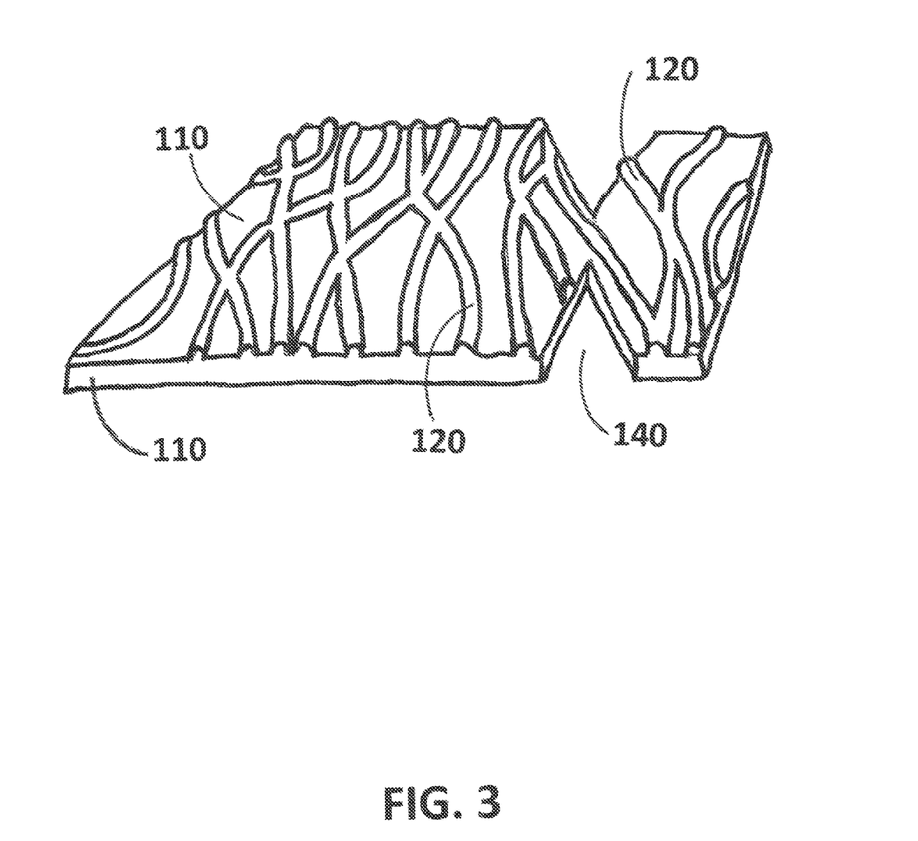
FIG. 3 depicts one embodiment of thermal therapy sheet with a cut made by a user.

FIG. 3 depicts one embodiment of thermal therapy sheet 100 cut 140 before applying to a bent joint. Thermal therapy sheet 100 may be applied to a joint area without cutting and is still comfortable. Cutting the embodiment is a method of user's choice or cut 140 may be manufactured in a predetermined size and shape.

Figure 4:
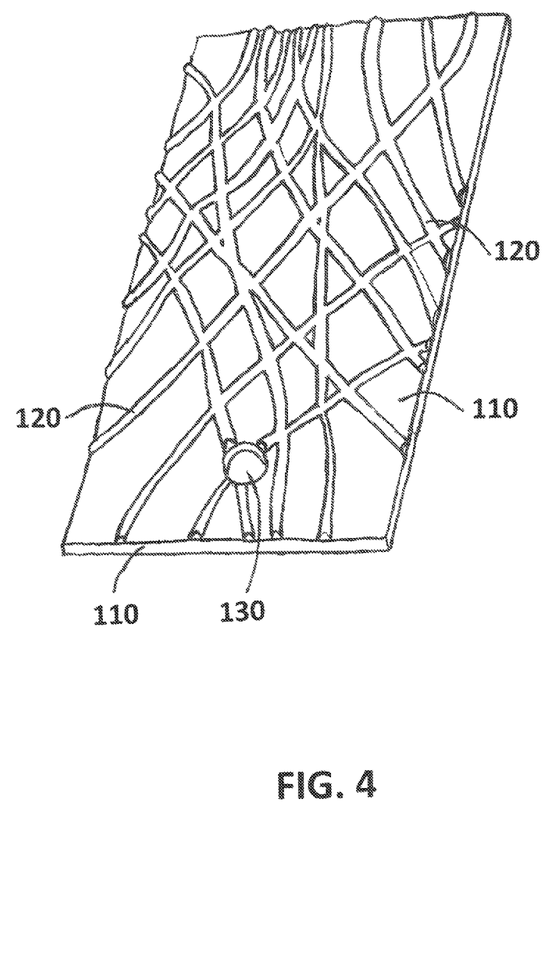
FIG. 4 depicts one embodiment of thermal therapy sheet having a cut thumb hole.

FIG. 4 depicts one embodiment of thermal therapy sheet 100 having cut a hole 130. Cut hole 130 may be more accommodating to a thumb when the thermal therapy sheet 100 is applied to a hand and cutting the hole 130 is to the discretion of user. As a nonlimiting example, hole 130 may be cut by user or hole 130 may be manufactured into thermal therapy sheet 100 at a predetermined location.

Figure 5A:
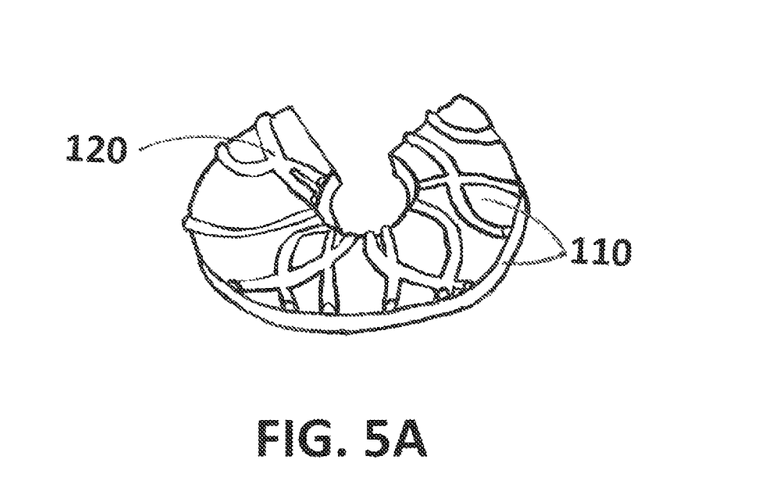
Figure 5B:
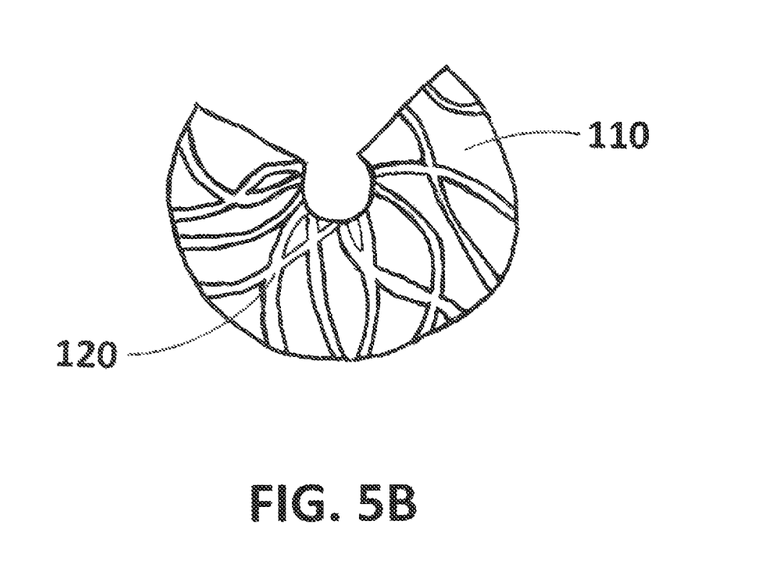

FIG. 5 A-B depicts a perspective view and top view of one embodiment of thermal therapy sheet 100 cut by a user for placement between a bra and human breast. As a nonlimiting example, the thermal therapy sheet 100 may be manufactured in a predetermined size and shape. Then, a user may cut a predetermined size and shape to better accommodate user's specific size breast.

Figure 6:
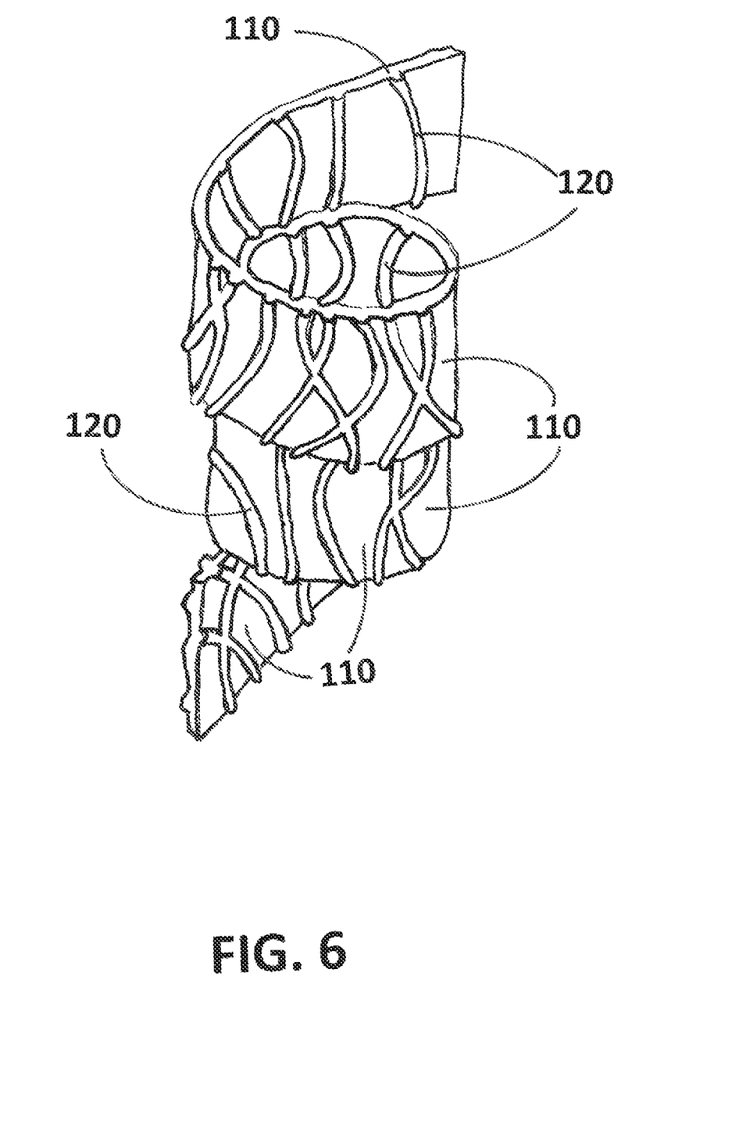
FIG. 6 depicts one embodiment as a rolled bandage with ridges on both sides of thermal therapy sheet 100.

FIG. 6 is a perspective of one embodiment of thermal therapy sheet 100 in the shape of a rectangular strip, but wrapped to form a bandage, and the orientation of ridges 120. Ridges 120 can be applied to both sides of the flexible thermal sheet 110, either as a sheet or rolled bandage. When the ridges 120 are applied to both sides of the flexible thermal sheet 110, it can create a lock where the device overlaps itself and then pressure is applied.

Figure 7:
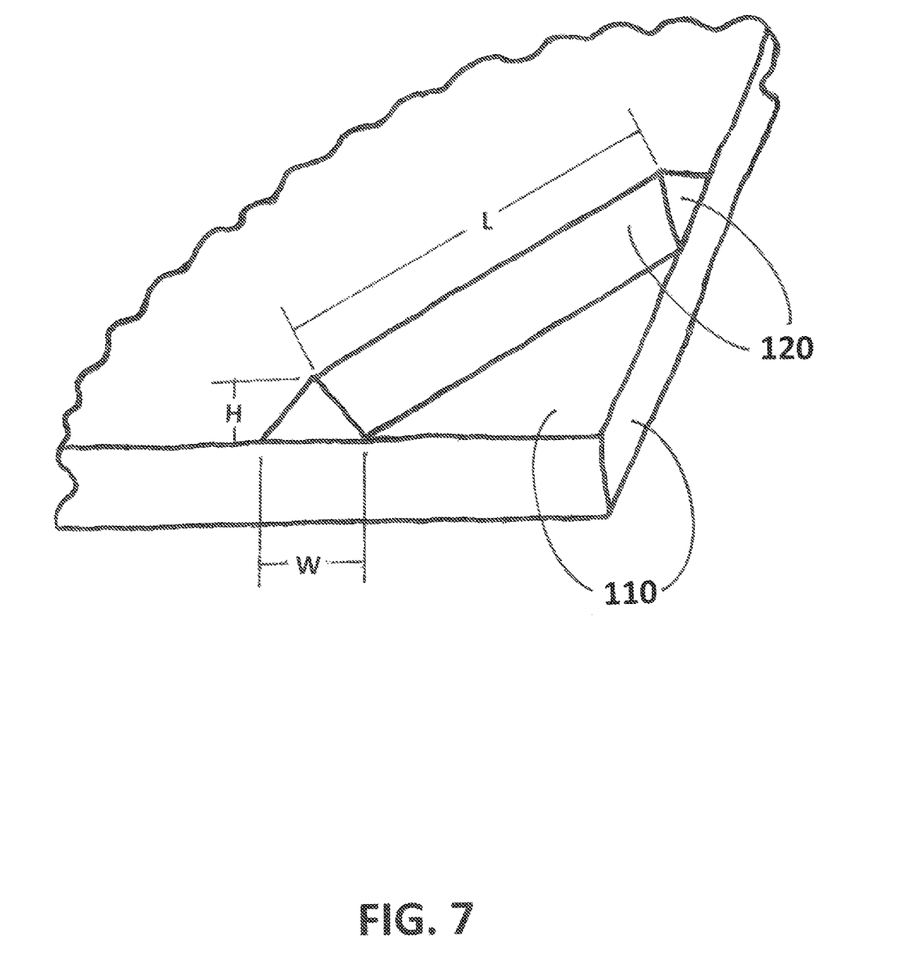
FIG. 7 perspective view of one embodiment of ridge 120, illustrating the dimensions of a ridge.

FIG. 7 is a perspective view of one embodiment of ridge 120. Depicted ridge 120 has length notated by L, width notated by W, and height notated by H. Ridges may be of various sizes and shapes. It is possible for ridge 120 to have the same length, width, or height. The variations of length, width, height are immense.

Thermal therapy sheet 100 may be used for multiple applications or sized and cut to each particular application. As a nonlimiting example, a 24 inch by 28 inch thermal therapy sheet 100 may be cut to a 12 inch by 28 inch, then wrapped around a thigh or knee. If thermal therapy sheet 100 is too large, it can be cut to size. The remaining piece may be applied to a wrist. The same 12 inch by 28 inch thermal therapy sheet 100 may be wrapped around an elbow multiple times or cut in half and wrapped around two separate elbows. Thermal therapy sheet 100 may be stretched providing compression to a selected body area. Thermal therapy sheet 100 may be cut small to be applied to a small selective area.

The advantages of this device include, without limitation:
use as a multipurpose devise;
use on multiple selected body areas of any size user;

no electricity;
self-heating, no prior heating is required;
portability;
sizing for a particular application, by cutting;
reusability;
use in conjunction with existing medical devises;
use on non-humans as well.

The benefits from the device mentioned above may be used as a figure molding and weight loss aid system, in the field of Angiology, and in the delivery of medications and creams.

Descriptions of known materials and manufacturing techniques may be omitted so as not to unnecessarily obscure the disclosure in detail.

While particular embodiments of the present invention have been illustrated and described, it will be obvious to those skilled in the art that various changes and modifications may be made without departing from the spirit and scope of the invention. The invention should therefore not be limited by the above described embodiment, method, drawings, examples, but by all embodiments and methods within the scope and spirit of the invention.

REFERENCE MATERIAL

"Thermal Comfort" by B. W. Olesen, Ph.D.
"Thermal Conductivity Of Some Common Materials and Gases" by The Engineeerring ToolBox http://www.engineeringtoolbox.com/thermal-conductivity

What is claimed is:

1. A device comprising:
   a. a sheet of material having a body including a top surface, a bottom surface and a circumferential sidewall, the body made of elastomeric flexible heat reradiating thermal material selected from the group consisting of silicone rubber, styrene butadiene, chloroprene, natural rubber and thermoplastic elastomer;
   b. the body having a thickness from approximately 0.025 inch to approximately 0.100 inch;
   c. a plurality of top elongated shaped acupuncture ridges integrally formed onto said top surface, a portion of the plurality of top elongated shaped acupuncture ridges formed in a crisscross pattern, the plurality of top elongated shaped acupuncture ridges randomly spaced on said top surface and extending transversely to said top surface;
   d. a plurality of bottom elongated shaped acupuncture ridges integrally formed onto said bottom surface, a portion of the plurality of bottom elongated shaped acupuncture ridges formed in a crisscross pattern, the plurality of bottom elongated shaped acupuncture ridges randomly spaced on said bottom surface and extending transversely to said bottom surface;
   e. each of said plurality of top and bottom elongated shaped acupuncture ridges is made of material selected from the group consisting of silicone rubber, styrene butadiene, chloroprene, natural rubber and thermoplastic elastomer; and
   f. said sheet of material formed into a rolled bandage;
   g. wherein the plurality of top elongated shaped acupuncture ridges and the plurality of bottom elongated shaped acupuncture ridges create a lock where the device overlaps itself and then pressure is applied.

2. A thermal therapy device for providing thermal therapy and compression to a body comprising:
   a. a sheet of material having a body including a top surface, a bottom surface and a circumferential sidewall, the body made of elastomeric flexible heat reradiating thermal material selected from the group consisting of silicone rubber, styrene butadiene, chloroprene, natural rubber and thermoplastic elastomer, wherein the sheet of material is configured to surround a portion of the body and conform to the body to relieve swelling and reduce aches and pains to joints, muscles, and other body parts via thermal therapy and compression;
   b. the body having a thickness from approximately 0.025 inch to approximately 0.100 inch;
   c. a plurality of top elongated shaped acupuncture ridges integrally formed onto said top surface, a portion of the plurality of top elongated shaped acupuncture ridges formed in a crisscross pattern, the plurality of top elongated shaped acupuncture ridges randomly spaced on said top surface and extending transversely to said top surface;
   d. a plurality of bottom elongated shaped acupuncture ridges integrally formed onto said bottom surface, a portion of the plurality of bottom elongated shaped acupuncture ridges formed in a crisscross pattern, the plurality of bottom elongated shaped acupuncture ridges randomly spaced on said bottom surface and extending transversely to said bottom surface; and
   e. each of said plurality of top and bottom elongated shaped acupuncture ridges is made of material selected from the group consisting of silicone rubber, styrene butadiene, chloroprene, natural rubber and thermoplastic elastomer.

3. A thermal therapy device for providing thermal therapy and compression to a body comprising:
   a. a sheet of material having a body including a top surface, a bottom surface and a circumferential sidewall, the body made of elastomeric flexible heat reradiating thermal material selected from the group consisting of silicone rubber, styrene butadiene, chloroprene, natural rubber and thermoplastic elastomer, wherein the sheet of material is configured to surround a portion of the body and conform to the body to relieve swelling and reduce aches and pains to joints, muscles, and other body parts via thermal therapy and compression;
   b. the body having a thickness from approximately 0.025 inch to approximately 0.100 inch;
   c. a plurality of elongated shaped acupuncture ridges integrally formed onto said top surface, a portion of the plurality of elongated shaped acupuncture ridges formed in a crisscross pattern, the plurality of elongated shaped acupuncture ridges randomly spaced on said top surface and extending transversely to said top surface; and
   d. each of said plurality of elongated shaped acupuncture ridges is made of material selected from the group consisting of silicone rubber, styrene butadiene, chloroprene, natural rubber and thermoplastic elastomer.

4. The device in accordance with claim 3, further comprising:
   a. a hole extending from the top surface to the bottom surface through the sheet of material; and
   b. wherein the hole facilitates insertion of an object through the hole to enable wrapping said sheet of material around an object.

5. The device in accordance with claim 3, further comprising: a cut in at least a portion of the sidewall of the sheet of material extending from the top surface to the bottom surface; and
   a. wherein the cut facilitates wrapping said sheet of material around an object.

6. A system for providing thermal therapy and compression to a body comprising:
   a. thermal therapy device of claim 3 and an external holding device being configured to press and hold the thermal therapy device against the body in order to relieve swelling and reduce aches and pains to joints, muscles, and other body parts via therapy and compression.

* * * * *